United States Patent [19]

Niegisch

[11] 4,278,623

[45] Jul. 14, 1981

[54] ULTRA-FINE FIBERS AND METHOD FOR MAKING SAME

[75] Inventor: Walter D. Niegisch, Watchung, N.J.

[73] Assignee: Union Carbide Corporation, New York, N.Y.

[21] Appl. No.: 758,424

[22] Filed: Jan. 11, 1977

[51] Int. Cl.³ .............................................. B29B 1/02
[52] U.S. Cl. ...................................... 264/28; 264/140
[58] Field of Search ................................. 264/28, 140

[56] References Cited

U.S. PATENT DOCUMENTS 2,307,371  1/1943  Hileman .................................. 264/28

OTHER PUBLICATIONS

American College Dictionary, Random House, N.Y. 1970, p. 242, "comminute".

Primary Examiner—Thomas P. Pavelko
Attorney, Agent, or Firm—Gerald R. O'Brien, Jr.

[57] ABSTRACT

Ultra-fine fibers, having an average diameter typically in the range of 0.1 to 5 micrometers, are provided which are capable of being dispersed in a liquid medium, such as a freeze dry liquid, to form a free-flowing, non-agglomerating slurry which may be employed to coat a substrate, as to provide an intimal lining for a circulatory assist device. Such ultra-fine fibers are prepared by immobilizing longer fibers in a medium, such as ice, and thereafter shearing the medium with the longer fibers embedded therein at a rate and for a time sufficient to comminute the fibers into appropriately short lengths.

9 Claims, 8 Drawing Figures

ULTRA-FINE FIBERS AND METHOD FOR MAKING SAME

This invention relates to ultra-fine fibers and, more particularly, to a method for processing such fibers into sufficiently short lengths to allow the preparation of a free-flowing, non-agglomerating slurry.

Techniques for preparing ultra-fine fibers are known, such fibers being often described as having diameters ranging from about 0.01 to about 1 to 5 micrometers. Thus, U.S. Pat. No. 3,099,067 discloses the co-extrusion of mutually immiscible thermoplastic materials, followed by the extraction or removal of one component. Similarly, U.S. Pat. No. 3,843,974 describes the preparation of ultra-fine fibers by forming a melt immiscible blend of a polyolefin and an ethylene/acrylic acid copolymer which is subjected to longitudinal drafting after the melt extrusion of the two incompatible thermoplastics. After drafting, the ethylene/acrylic acid copolymer is removed by a suitable solvent.

These ultra-fine fibers may be advantageously utilized for many applications, including blood compatible intimal linings for circulatory assist devices. In such applications, three-dimensional fibrous webs or networks formed from ultra-fine fibers are designed to provide a substrate for infiltration by cells which will develop into a securely anchored living lining of healthy tissue (neointima) on the surface of a prosthesis to prevent thrombosis and other complications associated with blood/polymer interactions. Thus, such linings find use on the walls of artificial hearts and other circulatory assist devices within and without the body, such as arterial prosthesis and linings for blood pumps. Such circulatory assist devices are fashioned from a pump means with associated inlet and outlet valves and means for connecting the pump to a human arterial blood supply containing at least in the pump chamber a non-porous elastomeric substrate with an intimal lining consisting of a vertically expanded ultra-fine fiber web of polypropylene fibers from about 10 to about 50 micrometers in depth and containing a substantial percentage of surface pores in the range of about 20 to 100 micrometers and in which the fibers typically have an average fiber diameter of about 0.05 to about 1.0 micrometer or so.

One difficulty which has been experienced in utilizing such ultra-fine fibers is that the prior techniques yield a web of such fibers which are composed of nearly infinite length networks of the fibers. This has limited, to some extent, the utility of these ultra-fine fibers. Thus, for example, the lining of a substrate with a complex shape has been, at best, difficult to achieve. Moreover, the handleability or processability of such long fibers is less than optimum, requiring tedious and lengthy manual operations in lining any substrate.

While these long ultra-fine fibers can be subdivided to shorter lengths by conventional chopping techniques employed with fibers of larger diameters, the resulting ultra-fine fibers are not of sufficiently short lengths to allow dispersing in a liquid diluent to form a free-flowing, non-agglomerating slurry. Moreover, in conventional fiber chopping techniques, care must be taken to avoid fusing of the cut fibers as the cutting blades dull and become heated. Such fused fibers typically cannot be separated.

It is accordingly an object of the present invention to provide ultra-fine fibers of sufficiently short lengths to allow the fibers to be dispersed into a liquid diluent to form a free-flowing, non-agglomerating slurry.

A further object provides a method of processing relatively long ultra-fine fibers into fibers of sufficiently short length that a free-flowing, non-agglomerating slurry of the fibers may be prepared.

A still further object of the present invention lies in the provision of ultra-fine fibers capable of being processed without the need to resort to tedious and/or lengthy manual operations. A related and more specific object provides ultra-fine fibers which can be used to coat or line substrates having complex shapes or surfaces.

Yet another object of this invention is to provide a process using ultra-fine fibers which is versatile and allows the properties of the fiber product to be readily controlled.

Another object lies in the provision of a process using ultra-fine fibers which is amenable to larger scale operations.

Other objects and advantages will be apparent from the following description and from the drawings, in which.

Figure 6:
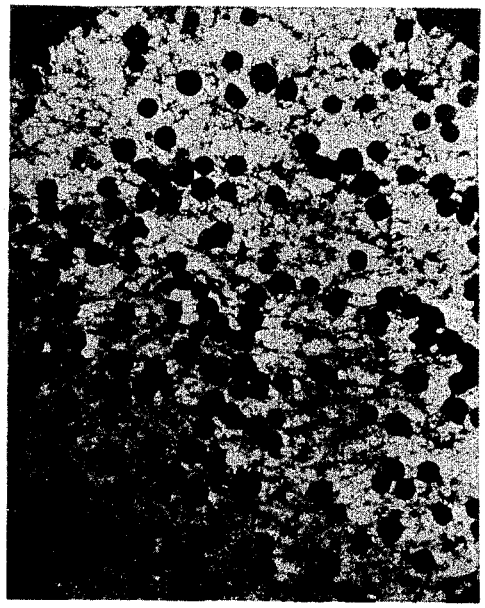
Figure 7:
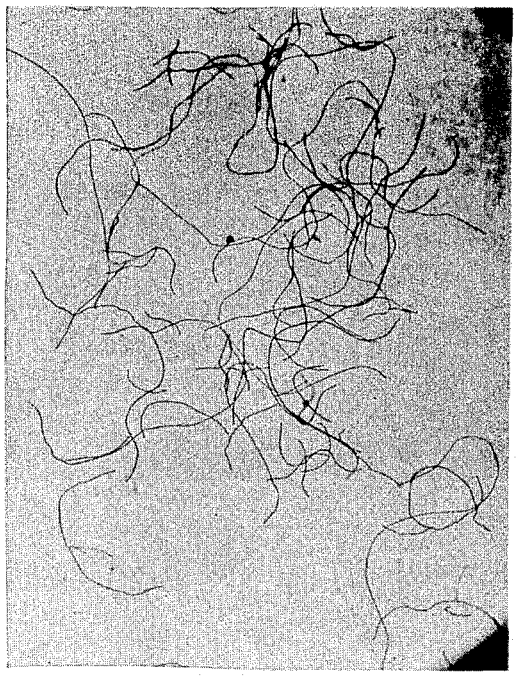
Figure 8:
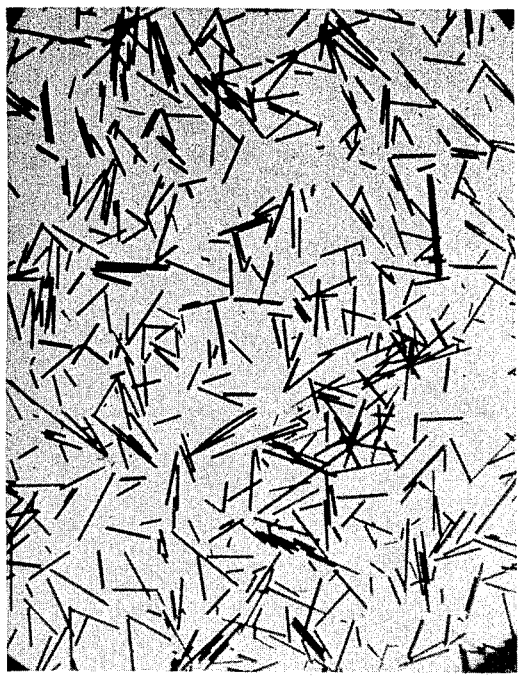

FIG. 6 is a photomicrograph at about 40×magnification and illustrates a fiber network of the ultra-fine fibers after use as an unsupported filter; and FIGS. 7 and 8 are photomicrographs at about 45×magnification and show, respectively, ultra-fine polyethylene terephthalate and graphite fibers which have been processed in accordance with the present invention.

While the invention is susceptible of various modifications and alternative forms, specific embodiments thereof have been shown by way of example and will hereinafter be described in detail. It should be understood, however, that it is not intended to limit the invention to the particular forms disclosed, but, on the contrary, the intention is to cover all modifications, equivalents and alternatives falling within the spirit and scope of the invention as expressed in the appended claims.

In general, the present invention is predicated on the discovery that the relatively long ultra-fine fibers produced by prior techniques can be comminuted into sufficiently short fibers to allow the preparation of a free-flowing, non-agglomerating slurry by first immobilizing the relatively long ultra-fine fibers in a suitable medium to embed the fibers therein and thereafter subjecting the immobilized fibers to shear at a rate and for a time sufficient to comminute the fibers into the desired lengths. Thereafter, the comminuted fibers may be processed as is needed for the particular intended application.

With respect to the material from which the ultra-fine fibers are formed, it is preferred to employ polypropylene, particularly when the comminuted ultra-fine fibers are to be used as an intimal lining for a circulatory assist device. However, any other material may be employed for the fibers, provided that the fiber can be subjected to shear below its softening point. The requirements of the end use, as well as economics, may well dictate the material utilized.

Suitable materials for forming the fibers are set forth in U.S. Pat. No. 3,099,067 and include such fiber-forming thermoplastic resins as polyethylene, polystyrene, alkyl and halogen-substituted styrenes, methacrylic ester polymers such as polymethylmethacrylate, vinyl ester polymers such as polyvinylacetate and polyvinylbutyrate, vinyl halide polymers such as polyvinylchloride, polyamides such as the nylons, fluorovinyl polymers such as polytrifluorochloroethylene, copolymers of styrene such as styrene and acrylonitrile copolymers, copolymers of vinyl halides and vinyl esters such as a copolymer of vinyl chloride and vinyl acetate, and copolymers of vinylidene halides and vinyl halides such as a copolymer of vinylidene chloride and vinyl chloride. Still further useful materials are identified in U.S. Pat. No. 3,914,501 and include polyethylene oxide, polyepsiloncaprolactone, wholly aliphatic polyester and polycarbonate resins, elastomeric polyurethanes, polyalkylacrylates, and the like. Useful materials are also set forth in U.S. Pat. Nos. 3,843,974 and 3,097,991.

In addition to thermoplastic materials of the types described herein, the present invention may also be utilized in connection with any of the many known inorganic materials from which fibers can be made. Thus, as illustrative examples, carbon and glass fibers may be processed according to this invention.

To provide the relatively long networks of ultra-fine fibers for use in the present invention, any of the known prior techniques may be employed which will provide fibers with the requisite diameter for the intended end use application. Useful ultra-fine fibers for many applications will typically have an average diameter of from about 0.05 to about 5 micrometers, often having an average diameter of less than about 2.5 micrometers or even less than about 1 micrometer. Suitable techniques for forming such fibers from thermoplastic materials are described in U.S. Pat. Nos. 3,099,067 and 3,843,974, previously identified. Techniques for forming fibers from inorganic materials are likewise well known.

In addition, the ultra-fine fibers can be obtained from processes which are principally directed to different applications. Thus, for example, artificial suede materials are available. In general, these comprise a semi-oriented mat of polyester fiber bundles impregnated with a polyurethane foam. As a source of ultra-fine fibers, it is suitable to utilize the polyester fibers of such materials; and these fibers can be obtained from the material by conventional separation techniques.

While the present invention perhaps finds its most advantageous utility in connection with ultra-fine fibers of particularly small diameters, it should be understood that the applicability is not so limited. The present invention is thus useful in connection with fibers having diameters up to 20 micrometers or more and, indeed, may be utilized with any fibers that cannot be satisfactorily processed by conventional fiber chopping techniques.

In accordance with the process of the present invention, the relatively long ultra-fine fibers are initially placed in an immobilizing medium and then immobilized, embedding the fibers therein. The immobilizing medium may be a liquid or a solid, a prime requirement being that the medium be capable of being removed from the fibers after completion of the requisite processing without degrading or otherwise adversely affecting the fibers. Any liquid diluent may be utilized to embed the fibers, with water being desirable due to its ready availability as well as the fact that immiscible polymer techniques for forming ultra-fine fibers often utilize water as the extracting medium. Accordingly, sources of ultra-fine fibers in water are readily available, obviating the need to disperse the fibers in another diluent.

The immobilizing step can be accomplished by any known technique, suitably by freezing dry ice or liquid nitrogen. The important point is that the embedded fibers be sufficiently immobilized to provide the support needed in the subsequent steps of the process. In this connection, while impurities in the medium can be tolerated, the presence of significant impurities may diminish the effectiveness of subsequent processing due to the more complex crystalline morphology that can result. Functionally, this more complex crystalline morphology may diminish somewhat the support provided the fibers.

The thus embedded ultra-fine fibers are then subjected to shear at a rate and for a time sufficient to comminute the fibers to satisfactorily short lengths. High shear rates are desirable from the standpoint of productivity; however, the tolerable shear rate will be dependent upon the heat transfer rates involved. Thus, in this step, localized temperatures in the vicinity of the fibers must not exceed their softening point since these fibers are highly elongated. Otherwise, it is possible that the fibers would shrink in length and eventually ball up.

Many types of equipment are available which will provide the necessary rates of shear. The particular equipment selected may, in general, be dependent upon the medium used to immobilize the fibers as well as the scale of the operation. As one example, for small scale operation, it has been found suitable to employ a conventional Waring blendor. The time required to accomplish the desired shear will vary, depending upon the efficiency of the equipment employed. Typically, adequate comminution of the fibers can be accomplished in minutes; but longer times can be used, if desired. Also, if inadequate comminution results, the shearing step can be repeated after immobilizing the fibers.

The efficiency of the shearing step will likewise be dependent upon the density of fibers in the frozen liquid diluent. Satisfactory fiber densities for a particular type of equipment utilized for the shearing step can be readily determined by examining the fibers after completion of the shearing step. If desired, prior to immobilizing, the ultra-fine fibers may be transversely drafted to provide a more open structure and eliminate significant fiber bundles. Suitable transverse drafting may be accomplished by known techniques.

In addition, to insure that satisfactory support is provided for the fibers, it may be desirable to carry out part or all of the shearing step in an environment which insures that the fibers remain immobilized in the medium employed. In a Waring blendor, this can be achieved by precooling the blendor by charging dry ice before addition of the fibers.

In accordance with a preferred aspect of the process of this invention, a liquid heat transfer medium is provided during the shearing step to dissipate undesirable heat buildup. Indeed, when equipment such as a Waring blendor is employed to accomplish the requisite shear, satisfactory operation requires the presence of a liquid heat transfer medium.

Desirably, when a liquid is used as the immobilizing liquid, the liquid heat transfer medium should be at least partially miscible with the diluent. When water is employed as the diluent, it is desirable to utilize methanol as the heat transfer medium since this is a liquid at dry ice temperatures and is miscible with water.

The effectiveness of the immobilizing and shearing steps can be determined by forming a dilute slurry or suspension of the thus-comminuted fibers and visually observing whether the resulting slurry is free-flowing and non-agglomerating. If necessary, the steps may be repeated to further comminute the fibers.

A free-flowing, non-agglomerating slurry will be achieved when, on the average, the length to diameter ratio of the ultra-fine fibers is in the range of about 1,000 or less. Higher fiber densities in the slurry will require fibers with lower average length to diameter ratios to achieve the desired free-flowing character. The lengths of the fibers may vary over a wide range after shearing, but this is unimportant as long as the average lengths are as has been described.

Further treatment for the thus-processed fibers will depend upon the intended end use application. Indeed, the end use application may well determine the desired length to diameter ratio of the fibers. When strength considerations are involved, it is desirable to optimize the average fiber length to diameter ratio. For nylon and polyethyleneterephthalate fibers, as reported by Auspos and Winn, *Tappi*, September 1962, Vol. 45, No. 9, pages 741-744, maximum tensile strength is provided when the fiber length to diameter ratio is about 500, viz., 465 for nylon and 520 for polyethyleneterephthalate. Other applications might require higher ratios while ratios of as low as 200 or even lower might be useful for still other applications.

When the end use involves a planar fiber structure, as for example, a synthetic paper, the sheared ultra-fine fibers can be formed into a slurry and deposited as is desired by conventional techniques. On the other hand, it is essential in some applications to provide a three-dimensional network (i.e., a fiber density essentially the same in each of the three dimensions) of the ultra-fine fibers.

In this latter instance, this can be accomplished by dispersing the sheared fibers in a medium that may be removed, when necessary, without adversely affecting to any significant extent the three-dimensional character of the fiber network. To this end, when a liquid diluent is used as the immobilizing medium, this may be replaced after the shearing step by any known liquid freeze dry medium. Removal of the liquid diluent may be accomplished by conventional separation techniques such as, for example, solvent exchange and filtration. Suitably, the freeze dry medium should have a relatively high vapor pressure and a melting point near ambient temperatures so as to facilitate rapid freeze drying. It may also be desirable to use as a freeze dry medium a liquid which is less dense than the ultra-fine fibers being processed, so that the fibers will not float to the surface of the slurry. Miscibility of the freeze dry medium with the liquid diluent may be desired in some instances; but this is not essential, as a wholly immiscible medium could be used.

In accordance with a preferred aspect of the present invention, it has been found desirable to utilize t-butyl alcohol as the freeze dry medium. Its melting point at room temperature and high vapor pressure are conducive to rapid freeze drying. It is also miscible with water and methanol. Other liquids can likewise be employed, 1,4-dioxane being an example.

The substitution of the freeze dry medium for the liquid diluent and, if used, the heat transfer medium, may be accomplished, as has previously been alluded to, by conventional techniques. As an illustrative example, after reaching ambient conditions, the sheared fibers in the diluent may optionally be first filtered to concentrate the slurry, removing up to about 90% or so of the volume of the liquid diluent. Additional diluent may then be removed by solvent exchange techniques. Minor amounts of the liquid diluent and/or heat transfer medium may remain, and amounts up to about 5% by volume or so do not adversely affect the freeze drying to any significant extent. Indeed, larger amounts of such liquids may perhaps be tolerated; but this may detract to some extent from the facile nature of the freeze drying step.

If desired, recovery of the sheared fibers may be somewhat simplified by utilizing a freeze dry medium as the immobilizing medium for the long fibers prior to shearing. Thus, the fibers, wetted with a freeze dry medium such as t-butyl alcohol, could be frozen using liquid nitrogen, sheared, and the liquid nitrogen thereafter allowed to evaporate. This leaves, after ambient temperatures are reached, the sheared fibers dispersed in the freeze dry medium.

The slurry of ultra-fine fibers in the freeze dry medium may then be applied to any desired substrate by freezing the slurry. Thereafter, the freeze dry medium is removed by conventional freeze drying. In this fashion, the remaining ultra-fine fibers comprise an open, relatively uniform three-dimensional network, as can be seen from conventional stereo images of scanning electron photomicrographs.

Providing the desired thickness of the fiber network is achieved by controlling the thickness of the slurry which is frozen onto the substrate, as well as the fiber density in the slurry. As may be appreciated, achieving a particular network thickness will require applying a slightly thicker layer of slurry. The extra thickness required will lessen as the fiber density in the slurry is increased. There is also a minimum slurry thickness that should be considered when homogeneity of the fiber network is a prime concern. Thus, to enhance homogeneity, the slurry thickness should be at least slightly in excess of the average length of the dispersed fibers.

The fibers of the resulting three-dimensional network may then be bonded together by use of an adhesive, removed from the substrate and manually applied to a further substrate. Alternatively, and preferably, the substrate on which the web is formed will be the substrate for the intended use. In the case of an intimal lining for a circulatory assist device, the substrate will typically be elastomeric or a polyurethane. Desirably, in this instance, the adhesive coating will not only bond the ultra-fine fibers together but will also bond the fibers to the substrate. As should be appreciated, the particular adhesive or bonding agent selected will generally depend upon the end use application. When a three-dimensional network is desired, the adhesive should be selected so as not to unduly reduce the porosity or compress the network.

It is preferred to utilize parylene polymers, i.e., poly-p-xylylene or poly-chloro-p-xylylene, as the adhesive. These polymers may be deposited on the fibers by vapor vacuum sublimation techniques, forming a coherent conformal coating which can be made pin-hole free in films as thin as 250 Å units. Vapor deposition of a parylene film on the fibers results in an encapsulation of each fiber in a parylene sheath as well as the formation of a continuous parylene film in the interface of an impermeable substrate, such as silicone rubber or polyurethane. U.S. Pat. Nos. 3,288,728 and 3,342,754 further disclose the parylene polymers and their use.

A preferred fiber bonding agent is Parylene C, a poly-chloro-p-xylylene (Union Carbide Corporation). A coating of this bonding agent results in only a very small loss in porosity of the web yet will typically provide the necessary adhesion and reinforcement.

Thus, as may be appreciated, the relative short length ultra-fine fibers formed in accordance with the present invention allow the formation of a free-flowing, non-agglomerating slurry capable of coating substrates, even those with complex surfaces or shapes, without the need to resort to tedious manual operations, yet providing, where three-dimensional networks are needed, the desired open structure. This also allows the ready repairing or patching of, or adding to, previously formed networks.

The ability to prepare a free-flowing, non-agglomerating slurry makes it possible to form fiber products on a large scale in at least a semi-continuous fashion. The product characteristics can also be closely controlled by selection of the desired fiber density since the fiber weight added can be closely measured.

The slurry fiber density can vary within wide limits. Fiber consistencies may be typically varied from about 0.2% or even less up to about 1.2% or more. The upper fiber density may well be dictated by the tolerable viscosity since the slurry, at relatively high fiber consistencies, can reach a paste-like condition.

Characteristic of the free-flowing, non-agglomerating slurries of the present invention is the ability of the fibers to redisperse without appreciable agglomeration of the fibers together even after being stored for extended periods of time. Redispersal after a storage period of a year or so should typically be possible.

The following Examples are intended to be merely illustrative of the present invention and not in limitation thereof.

EXAMPLE 1

This Example illustrates the formation of a thin, three-dimensional network in accordance with the present invention.

About 100 milligrams of a transversely drawn polypropylene web (the fiber diameters being about 0.2 to 1 micrometer), wetted with water, were cut into 1 cm. squares and frozen by adding the cut squares to a methanol/dry ice suspension with tweezers, the wetted squares forming frozen chunks in the suspension. The chunks were collected and transferred to a rapidly stirring Waring blendor already charged with a methanol/dry ice suspension covering the blendor blades.

After three minutes, the contents of the blendor were removed; and an aliquot was added to excess t-butyl alcohol, the t-butyl alcohol comprising about 90% of the total volume. Following mixing, the suspension was cooled to −34 degrees C.; and the resulting viscous material was added in dropwise fashion to liquid nitrogen. The resulting solid particles were again sheared in the Waring blendor containing a methanol/dry ice suspension. Stirring was continued for 15 minutes, with occasional addition of dry ice.

Figure 1:
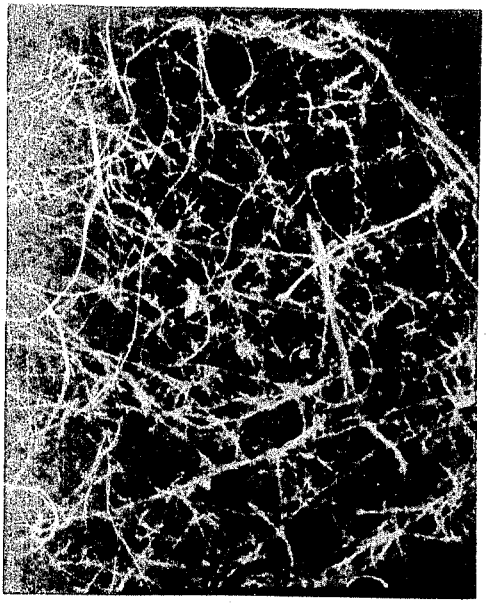
FIGS. 1 and 2 are photomicrographs at, respectively, about 600 and 1350×magnification, and illustrate a thin, three-dimensional fiber network formed from ultra-fine fibers processed in accordance with the present invention.
Figure 2:
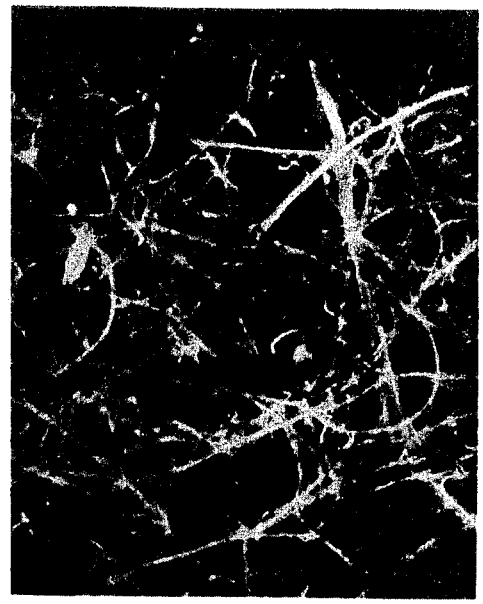

The resulting slurry was concentrated by filtration and exchanged three times with t-butyl alcohol so that the resulting freezing point was about +8 degrees C. From this, it was estimated that the methanol content of the slurry was about 5% by volume. A few drops of the resulting opalescent suspension, determined to contain about 0.14 grams per 5 c.c. of liquid (a fiber consistency of approximately 0.4%), were then freeze dried from liquid nitrogen directly onto the scanning electron microscope specimen stubs. The resulting structure is shown in FIGS. 1 and 2. A stereo pair image of FIG. 2 verified the three-dimensional fiber network.

Figure 3:
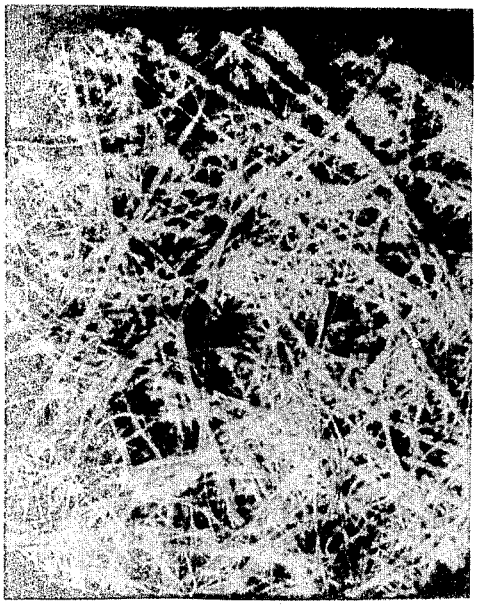
FIG. 3 is a photomicrograph at about 1350×magnification and shows a synthetic paper formed from the ultra-fine fibers.

A portion of the slurry was laid down without freeze drying; and a compact, paper-like network structure was obtained, as seen in FIG. 3. Stereo images showed that the fibers were compacted in the plane of the sheet.

EXAMPLE 2

This Example illustrates the use of the present invention in connection with the lining of a prosthesis.

A TECO Model #10 heart assist pump bladder was plugged (after charging) at each end with a stopper, and a syringe needle was inserted axially through the large stopper to provide a vent. Another needle was partially inserted in the other stopper, also axially. These needles served as a convenient spindle.

The bladder charge comprised six c.c. of an ultra-fine polypropylene fiber-n-butyl alcohol suspension having a fiber density of approximately 1 milligram per 10 c.c. The ultra-fine fibers were formed by freezing and shearing, as generally described in Example 1.

The bladder was rotated horizontally by hand while in contact with dry ice, using the axially amounted spindle. After about ten minutes, the contents were frozen on the inside of the bladder. The spindles were then removed, and the bladder was floated on liquid nitrogen and rotated occasionally over about a five-minute period. Finally, the bladder was stood vertically on its narrow end in a Denton Vacuum DV-515 evaporator. The large stopper was removed at this point, and vacuum was applied. No external cooling was provided. The bladder could be observed through the glass bell jar.

After about 30 minutes, evidence of sublimation was noted by the loss of frozen solvent at the open end. A large sheet of frozen suspension (about 12 cm.$^2$) separated from the inside surface of the bladder and settled at an angle of about 60 degrees from the vertical, supported at the bottom by the narrow neck of the bladder and at the top by leaning on the wall of the bladder. This solid sheet of suspension eventually freeze dried and afforded a continuous, freely suspended unsupported ultra-fine fiber network. The majority of the suspension clung to the walls and freeze dried with the most uniform web being formed near the open end of the bladder.

While cooling should have desirably been supplied during freeze drying, this could not be accomplished in the improvised freeze dry cell employed. However, sufficient areas were coated by the described procedure to demonstrate feasibility.

Figure 4:
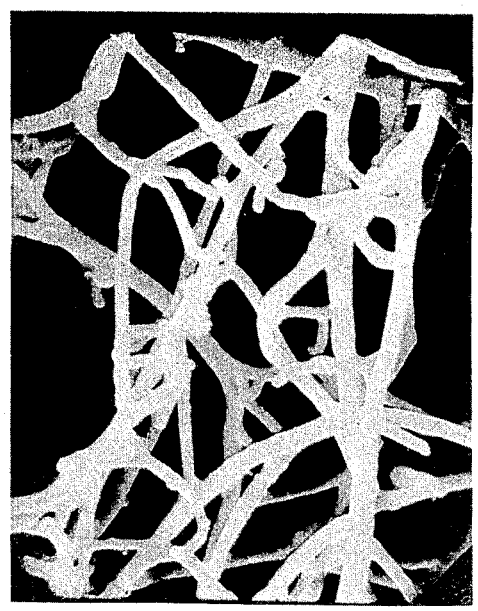
FIG. 4 is a photomicrograph at about 1350×magnification and illustrates a coated ultra-fine fiber network employed as an intimal lining in a heart assist pump bladder.

The bladder was then transferred to a conventional parylene deposition unit (described in *Encyclopedia of Polymer Science and Technology,* John Wiley and Sons, Inc., Vol. 15, page 100, 1971), where a film thickness of 0.43 micrometers of Parylene C was deposited, as determined by a glass witness strip (the coating on the glass strip being assumed to be of the same thickness as on the fibers). Scanning electron micrographs of a region of the bladder where the frozen web had adhered to the wall were made and are shown in FIG. 4. Stereo pairs established that the web was loosely packed and of a three-dimensional character. It was also visually evident that the coating of Parylene C had fused the web together at contact points where the fibers overlapped.

EXAMPLE 3

Figure 5:
FIG. 5 is a photomicrograph at about 7300×magnification and shows an unsupported ultra-fine fiber network coated with an adhesive.

To demonstrate the use of a fiber network formed from ultra-fine fibers processed in accordance with the present invention, the freeze dried and coated, freely suspended, unsupported network described in Example 2 (and shown in FIG. 5) was removed from the bladder and mounted with rubber cement on a washer having a one-half inch diameter opening. The utility of this three-dimensional network as a filter was demonstrated by filtering particles of Porasil with a size in the range of 75 to 125 micrometers dispersed in benzene.

After filtering, scanning electron micrographs were made of the unsupported network, the thickness of which was measured optically to be 100 micrometers. FIG. 6 illustrates the network after filtration of the particles, showing that the network adequately served as a filter.

EXAMPLE 4

This Example demonstrates the use of a three-dimensional network formed of ultra-fine fibers as a supported filter.

A few c.c. of an ultra-fine polypropylene fiber slurry, generally formed as was described in Example 1, were poured onto a stainless steel screen; and a random network of the fibers were supported by the screen. The utility of the composite construction as a filter was demonstrated by filtering a suspension of alumina particles of one micrometer suspended in benzene. Optical micrographs showed that the composite filter did in fact effectively filter the alumina particles from the benzene suspension.

EXAMPLE 5

This Example simulates the preparation of artificial blood vessels, utilizing the present invention.

A four inch length of ¾ inch diameter Tygon tubing having an inside diameter of one-half inch was charged with 1.6 c.c. of a polypropylene fiber slurry, generally formed as set forth in Example 1 and then plugged at each end as described in Example 2. The tube was cooled as was also described in Example 2 and was surrounded by a 766 gram metal heat sink precooled to about −196 degrees C. with liquid nitrogen. The system was evacuated after one stopper was removed.

It was observed that most of the liquid phase had apparently sublimed after about five hours, as indicated by a vacuum gage. The tube was removed from the heat sink after about 16 hours and was transferred to the parylene deposition unit described in Example 4 where a film of about 0.70 micrometers of Parylene C was deposited thereon, as determined from a glass witness strip.

The resulting deposit was examined by scanning electron microscopy, and it was observed that the ultra-fine fiber distribution was uniform but was somewhat less densely populated than had been anticipated. It was suspected that the freeze drying employed was inadequate, perhaps due to premature warming of the system before completion of sublimation.

However, this Example demonstrated the ability to deposit an essentially monofiber thick layer on a substrate.

EXAMPLE 6

This Example illustrates the formation of ultra-fine polyethylene terephthalate fibers in accordance with this invention.

A commercially available "Ultrasuede" material, comprising a mat of polyethylene terephthalate fibers, embedded in a polyurethane matrix, were liberated from the matrix by dissolving the matrix in dimethyl sulfoxide. The extracted fibrous mat was cut up into squares of about ¼ inch (about 0.65 grams). and soaked in water. The fiber mat pieces were then placed onto a layer of dry ice to freeze, followed by placing in liquid nitrogen of super freeze.

The frozen fiber sections were then sheared in a Waring blendor, precooled with a slurry of about 250 c.c. n-propyl alcohol in dry ice. After about three minutes, the slurry/fiber mixture was removed from the blendor and allowed to come to room temperature.

The fibers were removed from the n-propyl alcohol by skimming them from the surface and filtering and then measured in a graduated cylinder, followed by washing twice with 100 ml. of t-butyl alcohol to insure an n-propyl alcohol content of less than 0.5%.

The fiber/t-butyl alcohol slurry was frozen by spreading in petri dishes and placed in dry ice. The resulting frozen disks were broken up into pieces of about ¼ inch and placed in a liquid nitrogen bath to super freeze. Shearing was again carried out in a Waring blendor as previously described. To maximize fiber shearing, the procedure was repeated.

After the third shearing step, the fibers were filtered and washed with t-butyl alcohol. The fiber density of the resulting slurry was determined to be 0.0734 gm/5 c.c. of the alcohol (corresponding to a fiber consistency of about 1.2%).

FIG. 7 illustrates that the fibers were satisfactorily sheared.

EXAMPLE 7

This Examples shows the use of the present invention with ultra-fine graphite fibers.

About 0.59 mgs. of relatively long graphite fibers were soaked in approximately 0.30 c.c. water, were transferred to a petri dish, and then frozen over dry ice. The resulting ice/fiber disk was broken up into pieces of about ¼ inch and placed into liquid nitrogen to super freeze.

A slurry of n-propyl alcohol (250 c.c.) and dry ice was prepared in a beaker and maintained at −70 degrees to −80 degrees C. This slurry was then transferred to a Waring blendor while running the blendor. The ice/fiber chips were added to the blendor after decanting off the liquid nitrogen. The blendor was run at high speed for three minutes.

The slurry with graphite fibers was poured off into a beaker and allowed to come to room temperature. The fibers were filtered and washed several times with t-butyl alcohol to effect a near 100% solvent exchange.

As seen in FIG. 8, the shearing action resulted in graphite fibers with relatively low length to diameter ratios.

The resulting slurries, following shearing in accordance with the present invention, have provided ultra-fine fibers of sufficiently short lengths that the slurries are free-flowing and non-agglomerating. In each of the Examples, the final sheared fibers/t-butyl alcohol slurries were ascertained to be free-flowing and non-agglomerating.

What is claimed is:

1. A method of shortening ultra-fine fibers having a length to diameter ratio sufficiently high to prevent forming a free-flowing, non-agglomerating slurry of such fibers in a liquid diluent into sufficiently short fiber lengths to allow formation of a free-flowing, non-agglomerating slurry which comprises placing ultra-fine fibers into a medium, immobilizing the medium to embed the fibers therein and subjecting the immobilized fibers to shear at a rate and for a time sufficient to shorten the embedded ultra-fine fibers into lengths allowing formation of a free-flowing, non-agglomerating slurry.

2. The method of claim 1 wherein said ultra-fine fibers are polypropylene.

3. The method of claim 1 wherein the medium is a liquid diluent and immobilizing is carried out by freezing the liquid diluent.

4. The method of claim 3 wherein the liquid diluent is water.

5. The method of claim 1 wherein the shearing step is carried out in the presence of a liquid heat transfer medium.

6. The method of claim 5 wherein the heat transfer medium is methanol.

7. The method of claim 3 wherein, after the shearing step, the liquid diluent is replaced by a liquid freeze dry medium.

8. The method of claim 7 wherein said freeze dry medium has a density less than that of the material from which the ultra-fine fibers are formed.

9. The method of claim 7 wherein said freeze dry medium is t-butyl alcohol.

* * * * *

UNITED STATES PATENT AND TRADEMARK OFFICE
CERTIFICATE OF CORRECTION

PATENT NO. : 4,278,623
DATED : July 14, 1981
INVENTOR(S) : Walter D. Niegisch

It is certified that error appears in the above—identified patent and that said Letters Patent is hereby corrected as shown below:

Col. 2, line 30, "1350X" should read --7300X--.

Col. 4, lines 42, 63 and 64, "blendor" should read --blender--.

Col. 5, line 2, "blendor" should read --blender--.

Col. 7, lines 61, 62 and 63, "blendor" should read --blender--.

Col. 8, line 2, "blendor" should read --blender--.

Col. 8, line 32, "fiber-n-butyl" should read --fiber-t-butyl--.

Col. 10, lines 23, 25, 38, 61 and 62, "blendor" should read --blender--.

Col. 2, after line 47, insert a paragraph as follows:
--Since all micrographs shown in the FIGS of the drawings were reduced in size in the printed patent, the actual magnifications of the micrographs there reproduced are seventy-six percent (76%) of the values listed in this Column 2.--

Signed and Sealed this

Tenth Day of November 1981

[SEAL]

Attest:

GERALD J. MOSSINGHOFF

Attesting Officer

Commissioner of Patents and Trademarks